US009149270B2

(12) United States Patent
Fogel

(10) Patent No.: US 9,149,270 B2
(45) Date of Patent: Oct. 6, 2015

(54) ENDOSCOPIC TISSUE APPOSITION DEVICE AND METHOD OF USE

(75) Inventor: Roberto Fogel, Caracas (VE)

(73) Assignee: Davol, Inc. (a C.R. Bard Company), Warwick, RI (US)

(*) Notice: Subject to any disclaimer, the term of this patent is extended or adjusted under 35 U.S.C. 154(b) by 780 days.

(21) Appl. No.: 13/455,675

(22) Filed: Apr. 25, 2012

(65) Prior Publication Data

US 2012/0215235 A1    Aug. 23, 2012

Related U.S. Application Data

(62) Division of application No. 11/074,668, filed on Mar. 9, 2005, now Pat. No. 8,172,857.

(60) Provisional application No. 60/604,687, filed on Aug. 27, 2004.

(51) Int. Cl.
*A61B 17/04*        (2006.01)
*A61B 17/062*       (2006.01)
(Continued)

(52) U.S. Cl.
CPC ......... *A61B 17/0469* (2013.01); *A61B 17/0482* (2013.01); *A61B 17/0625* (2013.01); *A61B 17/10* (2013.01); *A61B 2017/0417* (2013.01); (Continued)

(58) Field of Classification Search
CPC .. A61B 17/0469; A61F 5/0083; A61F 5/0086
USPC .................................. 606/144–148, 139, 232
See application file for complete search history.

(56) References Cited

U.S. PATENT DOCUMENTS 3,868,448 A    2/1975  Hahn et al.
4,133,315 A    1/1979  Berman
(Continued)

FOREIGN PATENT DOCUMENTS

EP    0 571 938 A3    12/1993
EP    0 571 938 B1     4/1999
(Continued)

OTHER PUBLICATIONS

English translation of Notice of Reasons for Rejection, dated Apr. 20, 2011, for Japanese Patent Application No. 2005-235335 (4 pages).
(Continued)

*Primary Examiner* — Todd Manahan
*Assistant Examiner* — Majid Jamialahmadi
(74) *Attorney, Agent, or Firm* — Wolf, Greenfield & Sacks, P.C.

(57) ABSTRACT

An endoscopic tissue apposition device that includes a vacuum chamber configured to securely hold a portion of tissue therein, the vacuum chamber being defined by a proximal wall and a distal wall opposite to the proximal wall. Working and vacuum channels are provided in communication with the vacuum chamber. A portion of tissue may be held in the vacuum chamber when vacuum is applied in the vacuum chamber through the vacuum channel. A carrier needle is disposed on a proximal side of the vacuum chamber and is longitudinally advanceable into and across the vacuum chamber, while a punch needle is disposed on a distal side of the vacuum chamber and is configured to receive the carrier needle therein. A hold and release mechanism holds and releases the punch needle to facilitate joining portions of tissue together.

12 Claims, 12 Drawing Sheets

US 9,149,270 B2
Page 2

(51) Int. Cl.
*A61B 17/10* (2006.01)
*A61B 17/06* (2006.01)

(52) U.S. Cl.
CPC . *A61B2017/0454* (2013.01); *A61B 2017/0458* (2013.01); *A61B 2017/0464* (2013.01); *A61B 2017/06028* (2013.01); *A61B 2017/06042* (2013.01); *A61B 2217/005* (2013.01)

(56) References Cited

U.S. PATENT DOCUMENTS

| | | | |
|---|---|---|---|
| 4,246,893 A | 1/1981 | Berson | |
| 4,403,604 A | 9/1983 | Wilkinson et al. | |
| 4,416,267 A | 11/1983 | Garren et al. | |
| 4,694,827 A | 9/1987 | Weiner et al. | |
| 4,739,758 A | 4/1988 | Lai et al. | |
| 4,763,647 A | 8/1988 | Gambale | |
| 4,803,985 A | 2/1989 | Hill | |
| 4,899,747 A | 2/1990 | Garren et al. | |
| 4,917,103 A | 4/1990 | Gambale et al. | |
| 4,922,923 A | 5/1990 | Gambale et al. | |
| 4,922,924 A | 5/1990 | Gambale et al. | |
| 5,031,636 A | 7/1991 | Gambale et al. | |
| 5,060,660 A | 10/1991 | Gambale et al. | |
| 5,063,935 A | 11/1991 | Gambale | |
| 5,080,663 A | 1/1992 | Mills et al. | |
| 5,084,061 A | 1/1992 | Gau et al. | |
| 5,144,959 A | 9/1992 | Gambale et al. | |
| 5,250,053 A | 10/1993 | Snyder | |
| 5,259,399 A | 11/1993 | Brown | |
| 5,327,914 A | 7/1994 | Shlain | |
| 5,336,229 A * | 8/1994 | Noda | 606/144 |
| 5,345,949 A | 9/1994 | Shlain | |
| 5,365,944 A | 11/1994 | Gambale | |
| 5,372,592 A | 12/1994 | Gambale | |
| 5,409,459 A | 4/1995 | Gambale | |
| 5,423,872 A | 6/1995 | Cigaina | |
| 5,425,709 A | 6/1995 | Gambale | |
| 5,474,565 A | 12/1995 | Trott | |
| 5,549,621 A | 8/1996 | Bessler et al. | |
| 5,571,116 A | 11/1996 | Bolanos et al. | |
| 5,665,376 A | 9/1997 | Russo | |
| 5,686,141 A | 11/1997 | Haldenby | |
| 5,792,153 A * | 8/1998 | Swain et al. | 606/144 |
| 5,820,571 A | 10/1998 | Erades et al. | |
| 5,827,241 A | 10/1998 | Douk et al. | |
| 5,868,141 A | 2/1999 | Ellias | |
| 5,868,760 A | 2/1999 | McGuckin | |
| 5,887,594 A | 3/1999 | LoCicero, III | |
| 5,910,105 A | 6/1999 | Swain et al. | |
| 5,938,668 A | 8/1999 | Scirica et al. | |
| 5,977,175 A | 11/1999 | Lin | |
| 6,009,877 A | 1/2000 | Edwards | |
| 6,044,846 A | 4/2000 | Edwards | |
| 6,083,150 A | 7/2000 | Aznoian et al. | |
| 6,092,528 A | 7/2000 | Edwards | |
| 6,102,922 A | 8/2000 | Jakobsson et al. | |
| 6,139,555 A | 10/2000 | Hart et al. | |
| 6,234,955 B1 | 5/2001 | Silverman et al. | |
| 6,238,335 B1 | 5/2001 | Silverman et al. | |
| 6,248,058 B1 | 6/2001 | Silverman et al. | |
| 6,248,112 B1 | 6/2001 | Gambale et al. | |
| 6,251,063 B1 | 6/2001 | Silverman et al. | |
| 6,251,064 B1 | 6/2001 | Silverman et al. | |
| 6,251,079 B1 | 6/2001 | Gambale et al. | |
| 6,277,082 B1 | 8/2001 | Gambale et al. | |
| 6,315,778 B1 | 11/2001 | Gambale et al. | |
| 6,398,795 B1 | 6/2002 | McAlister et al. | |
| 6,427,089 B1 | 7/2002 | Knowlton | |
| 6,428,548 B1 | 8/2002 | Durgin et al. | |
| 6,432,126 B1 | 8/2002 | Gambale et al. | |
| 6,447,522 B2 | 9/2002 | Gambale et al. | |
| 6,447,533 B1 | 9/2002 | Adams | |
| 6,458,092 B1 | 10/2002 | Gambale et al. | |
| 6,461,370 B1 | 10/2002 | Gray et al. | |
| 6,494,888 B1 | 12/2002 | Laufer et al. | |
| 6,517,527 B2 | 2/2003 | Gambale et al. | |
| 6,530,878 B2 | 3/2003 | Silverman et al. | |
| 6,533,717 B2 | 3/2003 | Silverman et al. | |
| 6,535,764 B2 | 3/2003 | Imran et al. | |
| 6,540,789 B1 | 4/2003 | Silverman et al. | |
| 6,543,456 B1 | 4/2003 | Freeman | |
| 6,558,400 B2 | 5/2003 | Deem et al. | |
| 6,572,629 B2 | 6/2003 | Kalloo et al. | |
| 6,575,896 B2 | 6/2003 | Silverman et al. | |
| 6,592,596 B1 | 7/2003 | Geitz | |
| 6,595,903 B2 | 7/2003 | Nerio et al. | |
| 6,595,910 B2 | 7/2003 | Silverman et al. | |
| 6,608,029 B1 | 8/2003 | Kolterman et al. | |
| 6,611,715 B1 | 8/2003 | Boveja | |
| 6,615,084 B1 | 9/2003 | Cigaina | |
| 6,627,206 B2 | 9/2003 | Lloyd | |
| 6,629,987 B1 | 10/2003 | Gambale et al. | |
| 6,656,182 B1 * | 12/2003 | Hayhurst | 606/232 |
| 6,663,639 B1 | 12/2003 | Laufer et al. | |
| 6,675,809 B2 | 1/2004 | Stack et al. | |
| 6,692,520 B1 | 2/2004 | Gambale et al. | |
| 6,709,425 B2 | 3/2004 | Gambale et al. | |
| 6,712,814 B2 | 3/2004 | Edwards et al. | |
| 6,716,222 B2 | 4/2004 | McAlister et al. | |
| 6,733,488 B2 | 5/2004 | Gambale et al. | |
| 6,749,607 B2 | 6/2004 | Edwards et al. | |
| 6,755,869 B2 | 6/2004 | Geitz | |
| 6,758,219 B2 | 7/2004 | Sapala et al. | |
| 6,773,440 B2 | 8/2004 | Gannoe et al. | |
| 6,773,441 B1 | 8/2004 | Laufer et al. | |
| 6,786,929 B2 | 9/2004 | Gambale et al. | |
| 6,802,858 B2 | 10/2004 | Gambale et al. | |
| 6,835,199 B2 | 12/2004 | McGuckin et al. | |
| 6,835,200 B2 | 12/2004 | Laufer et al. | |
| 6,845,776 B2 | 1/2005 | Stack et al. | |
| 6,846,312 B2 | 1/2005 | Edwards et al. | |
| 6,858,576 B1 | 2/2005 | Young et al. | |
| 6,916,332 B2 | 7/2005 | Adams | |
| 6,944,570 B2 | 9/2005 | Neeser et al. | |
| 6,955,643 B2 | 10/2005 | Gellman et al. | |
| 6,997,931 B2 | 2/2006 | Sauer et al. | |
| 7,033,373 B2 | 4/2006 | De la Torre et al. | |
| 7,037,315 B2 | 5/2006 | Sancoff et al. | |
| 7,037,344 B2 | 5/2006 | Kagan et al. | |
| 7,083,630 B2 | 8/2006 | DeVries et al. | |
| 7,090,684 B2 | 8/2006 | McGuckin et al. | |
| 7,125,413 B2 | 10/2006 | Grigoryants | |
| 7,153,314 B2 | 12/2006 | Laufer et al. | |
| 7,175,638 B2 | 2/2007 | Gannoe et al. | |
| 7,204,842 B2 | 4/2007 | Geitz | |
| 7,229,428 B2 | 6/2007 | Gannoe | |
| 7,431,725 B2 | 10/2008 | Stack et al. | |
| 7,503,922 B2 | 3/2009 | Deem et al. | |
| 7,510,559 B2 | 3/2009 | Deem et al. | |
| 7,520,884 B2 | 4/2009 | Swanstrom | |
| 7,666,195 B2 | 2/2010 | Kelleher et al. | |
| 7,691,152 B2 | 4/2010 | Silverman | |
| 7,704,264 B2 | 4/2010 | Ewers | |
| 7,736,372 B2 | 6/2010 | Reydel | |
| 7,736,373 B2 | 6/2010 | Laufer | |
| 7,737,109 B2 | 6/2010 | Miller | |
| 8,172,857 B2 | 5/2012 | Fogel | |
| 2001/0011543 A1 | 8/2001 | Forsell et al. | |
| 2002/0022851 A1 | 2/2002 | Kalloo et al. | |
| 2002/0055750 A1 | 5/2002 | Durgin et al. | |
| 2002/0065523 A1 | 5/2002 | McAlister et al. | |
| 2002/0082616 A1 | 6/2002 | McAlister et al. | |
| 2002/0107530 A1 | 8/2002 | Sauer et al. | |
| 2002/0115991 A1 | 8/2002 | Edwards | |
| 2002/0139379 A1 | 10/2002 | Edwards et al. | |
| 2002/0143346 A1 | 10/2002 | McGuckin et al. | |
| 2002/0169357 A1 | 11/2002 | Chen | |
| 2002/0183765 A1 | 12/2002 | Adams | |
| 2002/0183768 A1 | 12/2002 | Deem et al. | |
| 2002/0193816 A1 | 12/2002 | Laufer et al. | |
| 2003/0009165 A1 | 1/2003 | Edwards et al. | |
| 2003/0021822 A1 | 1/2003 | Lloyd | |
| 2003/0109892 A1 | 6/2003 | Deem et al. | |

(56) References Cited

U.S. PATENT DOCUMENTS

| | | |
|---|---|---|
| 2003/0113310 A1 | 6/2003 | Van Laere et al. |
| 2003/0139752 A1 | 7/2003 | Pasricha et al. |
| 2003/0158601 A1 | 8/2003 | Silverman et al. |
| 2003/0171760 A1 | 9/2003 | Gambale |
| 2003/0181925 A1* | 9/2003 | Bain et al. .............. 606/144 |
| 2003/0188755 A1 | 10/2003 | Milbocker |
| 2003/0195529 A1* | 10/2003 | Takamoto et al. ........... 606/145 |
| 2003/0208209 A1 | 11/2003 | Gambale et al. |
| 2003/0233108 A1 | 12/2003 | Gellman et al. |
| 2003/0236536 A1 | 12/2003 | Grigoryants et al. |
| 2004/0006351 A1 | 1/2004 | Gannoe et al. |
| 2004/0039452 A1 | 2/2004 | Bessler |
| 2004/0044353 A1 | 3/2004 | Gannoe |
| 2004/0044354 A1 | 3/2004 | Gannoe et al. |
| 2004/0059289 A1 | 3/2004 | Garza Alvarez |
| 2004/0082963 A1 | 4/2004 | Gannoe et al. |
| 2004/0087977 A1 | 5/2004 | Nolan et al. |
| 2004/0092892 A1 | 5/2004 | Kagan et al. |
| 2004/0097415 A1 | 5/2004 | Kolterman et al. |
| 2004/0097986 A1 | 5/2004 | Adams |
| 2004/0097989 A1 | 5/2004 | Molina Trigueros |
| 2004/0116949 A1 | 6/2004 | Ewers et al. |
| 2004/0117031 A1 | 6/2004 | Stack et al. |
| 2004/0122456 A1 | 6/2004 | Saadat et al. |
| 2004/0122473 A1 | 6/2004 | Ewers et al. |
| 2004/0133147 A1 | 7/2004 | Woo et al. |
| 2004/0158263 A1 | 8/2004 | McAlister et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0193190 A1 | 9/2004 | Liddicoat et al. |
| 2004/0193194 A1 | 9/2004 | Laufer et al. |
| 2004/0194157 A1 | 9/2004 | Meguid |
| 2004/0194790 A1 | 10/2004 | Laufer et al. |
| 2004/0199180 A1 | 10/2004 | Knodel et al. |
| 2004/0210243 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236356 A1 | 11/2004 | Rioux et al. |
| 2004/0258621 A1 | 12/2004 | Stern |
| 2004/0267378 A1 | 12/2004 | Gazi |
| 2005/0022827 A1 | 2/2005 | Woo et al. |
| 2005/0033319 A1 | 2/2005 | Gambale et al. |
| 2005/0033320 A1 | 2/2005 | McGuckin et al. |
| 2005/0043817 A1 | 2/2005 | McKenna |
| 2005/0049614 A1 | 3/2005 | Cendan |
| 2005/0055038 A1 | 3/2005 | Kelleher et al. |
| 2005/0065536 A1 | 3/2005 | Ewers et al. |
| 2005/0075653 A1 | 4/2005 | Saadat et al. |
| 2005/0080444 A1 | 4/2005 | Kramer et al. |
| 2005/0090837 A1 | 4/2005 | Sixto et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0149067 A1 | 7/2005 | Takemoto et al. |
| 2005/0149072 A1 | 7/2005 | DeVries et al. |
| 2005/0149200 A1 | 7/2005 | Silverman et al. |
| 2005/0171556 A1 | 8/2005 | Murphy |
| 2005/0177176 A1 | 8/2005 | Gerbi et al. |
| 2005/0216036 A1 | 9/2005 | Nakao |
| 2005/0251162 A1 | 11/2005 | Rothe et al. |
| 2005/0256587 A1 | 11/2005 | Egan |
| 2006/0020277 A1 | 1/2006 | Gostout et al. |
| 2006/0047289 A1 | 3/2006 | Fogel |
| 2006/0149316 A1 | 7/2006 | DeVries et al. |
| 2006/0212053 A1 | 9/2006 | Gertner |
| 2006/0282087 A1 | 12/2006 | Binmoeller |
| 2007/0032702 A1 | 2/2007 | Ortiz |
| 2007/0032800 A1 | 2/2007 | Ortiz et al. |
| 2007/0049929 A1 | 3/2007 | Catanese, III et al. |
| 2007/0055292 A1 | 3/2007 | Ortiz et al. |
| 2007/0129735 A1 | 6/2007 | Filipi et al. |
| 2007/0167963 A1 | 7/2007 | Deem et al. |
| 2007/0173931 A1 | 7/2007 | Tremulis et al. |
| 2007/0175488 A1 | 8/2007 | Cox |
| 2007/0219570 A1 | 9/2007 | Deem |
| 2008/0249538 A1 | 10/2008 | Kraemer et al. |
| 2009/0088780 A1 | 4/2009 | Shiono et al. |
| 2009/0088796 A1 | 4/2009 | Abbott et al. |
| 2010/0137885 A1 | 6/2010 | Ortiz |

FOREIGN PATENT DOCUMENTS

| | | |
|---|---|---|
| EP | 1 397 998 A1 | 3/2004 |
| EP | 1414378 B1 | 5/2004 |
| EP | 1 759 639 A1 | 3/2007 |
| EP | 1815805 B1 | 8/2007 |
| JP | 10-500318 A | 1/1998 |
| WO | WO 93/20819 A1 | 10/1993 |
| WO | WO 99/35987 A1 | 7/1999 |
| WO | WO 99/60931 A1 | 12/1999 |
| WO | WO 00/48672 A1 | 8/2000 |
| WO | WO 01/66020 A2 | 9/2001 |
| WO | WO 02/060328 A1 | 8/2002 |
| WO | WO 02/096327 A2 | 12/2002 |
| WO | WO 03/051391 A1 | 6/2003 |
| WO | WO 03/086247 A1 | 10/2003 |
| WO | WO 2004/017863 A2 | 3/2004 |
| WO | WO 2004/019765 A2 | 3/2004 |
| WO | WO 2004/084808 A2 | 10/2004 |
| WO | WO 2004/103189 A1 | 12/2004 |
| WO | WO 2004/112563 A2 | 12/2004 |
| WO | WO 2005/011463 A2 | 2/2005 |
| WO | WO 2005/011519 A2 | 2/2005 |
| WO | WO 2005/020802 A2 | 3/2005 |
| WO | WO 2005/037072 A2 | 4/2005 |
| WO | WO 2005/037152 A1 | 4/2005 |
| WO | WO 2005/039458 A2 | 5/2005 |
| WO | WO 2005/058239 A2 | 6/2005 |
| WO | WO 2009/042816 A2 | 4/2009 |
| WO | WO 2010/021743 A1 | 2/2010 |

OTHER PUBLICATIONS

Awan, et al., "Endoscopic Vertical Band Gastroplasty with an Endoscopic Sewing Machine" Gastrointestinal Endoscopy, vol. 55, No. 2, 2002 pp. 254-256.

Schweitzer, "Endoscopic Intraluminal Suture Plication of the Gastric Pouch and Stoma in Postoperative Roux-en-Y Gastric Bypass Patients" Journal of Laparoendoscopic & Advanced Surgical Techniques, vol. 14, No. 4, 2004, pp. 223-226.

US 6,331,185, 12/2001, Gambale et al. (withdrawn)

* cited by examiner

ENDOSCOPIC TISSUE APPOSITION DEVICE AND METHOD OF USE

RELATED APPLICATIONS

This application is a divisional of U.S. application Ser. No. 11/074,668, filed on Mar. 9, 2005, which claims the benefit of U.S. Provisional Application No. 60/604,687, filed on Aug. 27, 2004, each of which is incorporated herein by reference in its entirety.

FIELD OF THE INVENTION

The present application relates to an improved endoscopic apposition device and method of use for treating patients suffering from obesity and other such gastric ailments. Specifically, the invention provides an endoscopic apposition device configured to collect a plurality of stomach tissue portions and sew or suture the tissue portions together using the apposition device.

BACKGROUND OF INVENTION

Obesity arguably is one of the most serious health problems in the United States as well as the world, affecting millions of people of all ages. Apart from the physical and psychological effects, especially on the younger population, obesity predisposes individuals to serious diseases, such as coronary artery disease, hyperlipidemia, hypertension and diabetes mellitus. The costs to the health system in the United States alone are estimated to be over thirty-nine billion dollars per year.

Weight reduction can be achieved either by increasing caloric expenditures through exercise and/or by reducing caloric intake. Reducing caloric intake can be achieved in a number of ways, such as surgical procedures to reduce the stomach capacity or to reduce the food transit time in the gastrointestinal tract, by using appetite suppressants like amphetamines or noradrenergic compounds, or via other methods, such as introducing balloons into the stomach. The appetite suppressants act on the central nervous system and are associated with considerable morbidity and side effects. Balloon inserts have several disadvantages, which include failure due to bursting or dislodging, intestinal obstruction (blockage of the intestinal lumen), and a requirement of use of complicated devices and/or procedures to secure the balloon within the stomach.

Historically, numerous patents have been issued for devices and methods for treating obesity and other such gastric related ailments. For example, U.S. Pat. No. 4,899,747, issued Feb. 13, 1990, to Garren et al., discloses a method and apparatus for treating obesity. In particular, the apparatus is a flexible, free floating and unattached inflatable balloon that is inserted into the stomach. Upon insertion into the stomach, the balloon is then inflated to reduce the stomach volume of the patient. U.S. Pat. No. 4,694,827, issued Sep. 22, 1987 to Weiner et al., discloses another balloon based approach for treating obesity. In particular, the balloon, when inflated, has a plurality of smooth surfaced convex protrusions disposed in locations that permit the balloon to engage the stomach wall at specific locations.

U.S. Pat. No. 5,686,141, issued Feb. 9, 1999 to Y. A. Ellias, discloses an endoscopic stomach insert having a plurality of flexible blades coupled at one end thereof to a base portion and circumferentially arranged around the central axis of the base. A retainer is provided to releasably couple the distal portions of the blades within close proximity of each other.

U.S. Pat. No. 5,423,872, issued Jun. 13, 1995 to V. Cigaina, discloses a process for treating obesity involving the sequential application of electrical pulses to the stomach for preset periods of time. Another patent to V. Cigaina, i.e., U.S. Pat. No. 6,615,084 issued Sep. 2, 2003, discloses another technique for electro-stimulation of the lesser curvature of the stomach, most preferably on the lower or distal end of the lesser curvature, wherein the lesser curvature is stimulated at a rate of 2-14 pulses per minute.

U.S. Pat. No. 6,540,789, issued Apr. 9, 2003, to Silverman et al., discloses a method for treating morbid obesity involving at least one implant positioned in the wall near the pyloric sphincter to inhibit emptying of the stomach. In yet another example of an implantable device, U.S. Pat. No. 6,611,715, issued Aug. 26, 2003, to B. R. Boveja, discloses an apparatus and method for neuromodulation to treat obesity and compulsive eating disorders using an implantable lead-receiver and an external stimulator. The external stimulator emits electrical pulses that stimulate the vagus nerve. The external stimulator contains a power source, control circuitry, a primary coil, and predetermined programs to control the different levels of therapy.

U.S. Pat. No. 6,627,206, issued Sep. 30, 2003, to G. A. Lloyd, discloses a technique for treating obesity using a mechanism for the time release of medications. In particular, a plurality of space-filling portions are sized to be received within the patient's body, wherein the portions come together in the patient's body to form a structure that provides therapeutic benefits to the patient.

U.S. Pat. No. 6,535,764, issued Mar. 18, 2003 to Imran et al., discloses a device and method for diagnosing and treating gastric disorders. The device is positioned within the stomach of the patient and secured thereto by an attachment mechanism. The device can either be a sensor for sensing various parameters of the stomach or stomach environment or a therapeutic delivery device. In one embodiment, the device provides gastric electrical stimulation, wherein stimulating electrodes are secured to the stomach wall by the attachment mechanism. An electronics unit contains the electronic circuitry of the device, and the device is programmable to respond to the sensed information or signals. An endoscopic delivery system delivers the device through the esophagus into the stomach, wherein the device is attached to the stomach wall. Endoscopic instruments are then attached to the device and attachment mechanism and are used to assist in determining the optimal attachment location on the stomach wall.

U.S. Pat. No. 6,755,869, issued Jun. 29, 2004, to Geitz, discloses a prosthesis formed from a porous weave of bio-absorbable filaments having an open mesh configuration that is formed into an oblate shape having dimensions that are greater than the esophageal opening and gastric outlet of the stomach. The prosthesis is deployed in the stomach to limit the amount of food that may be held within the stomach as well as to apply pressure on the fundus, so as to create a sensation of being full.

Another example of a device for treating obesity and other such gastric ailments includes an elastic band installed around the external wall of the patient's stomach to reduce the internal volume thereof. As a result, the patient requires less food to achieve a sensation of being full and typically loses substantial amounts of weight in a relatively short period of time.

Yet another example of a device that is used to treat obesity and other such gastric ailments is the use of an endoscopic apposition device to sew or suture portions of a patient's stomach tissue together. U.S. Pat. No. 5,080,663, issued Jan.

14, 1992, to Mills et al., U.S. Pat. No. 5,792,153, issued Aug. 11, 1998, to Swain et al., as well as U.S. Patent Application Publication No. 2003/0208209, published Nov. 6, 2003, to Gamble et al., and WO Patent Application Publication No. 2004/103189, published Dec. 2, 2004, to Gamble et al., each disclose various types of endoscopic apposition devices.

Endoscopic apposition devices are used without having to make an external incision in the patient, and are controlled externally of the patient by endoscopic means. Apposition devices typically include a sewing or stapling device for use with a flexible endoscope, although endoscopic apposition devices can also be used with a rigid endoscope.

For example, to stitch or sew together certain portions of stomach tissue, the apposition device, such as a sewing capsule, is attached to the end of a viewing endoscope and inserted through the esophagus of a patient to form a plurality of stitches in stomach tissue slightly below the lower end of the esophagus. A first stitch is made through stomach tissue to one side of the esophagus, and a second stitch is made, with the same suture thread, in stomach tissue adjacent to the first stitch. The two stitches are then drawn together to pull together the diametrically opposed, stitched stomach portions.

After the sutures are applied, the endoscope is removed from the patient and a knot is tied with the free ends of the suture thread that extend outside of the patient. The knot is pushed down to the site of the sutures by a thread guide device that has been positioned at the distal end of the endoscope. The suturing and knotting procedure is repeated several times. After a sufficient number of knots and sutures have been placed, a thread cutter, also operable through the endoscope, is used to cut the suture thread at points that are close to the tissue.

In general, the '663 patent to Mills et al. and the '153 patent to Swain et al. disclose a sewing device positioned on the distal end of an endoscope and used to pass a thread through a portion of stomach tissue. The sewing device includes a hollow needle movable between a first position in which the needle is out of the stomach tissue and a second position in which the needle passes through the portion of stomach tissue, and a thread carrier that is attached to the thread and is received within the needle. The sewing device also includes a body, which defines a cavity within which the portion of stomach tissue is held by a suction force, and within which the needle is mounted for movement between first and second positions.

A more particular or specific description of how the conventional endoscopic appositions devices operate will now be provided using the device disclosed by the '153 patent to Swain et al. as an example. The description of how the device disclosed by the '153 patent to Swain et al. operates will also be instrumental in understanding the differences with the operation and the present invention, which will be described in detail below.

FIGS. 1-3 illustrate the conventional endoscopic apposition device disclosed in the '153 patent to Swain et al.

FIG. 1 shows the distal end of a flexible endoscope 1, on which a sewing device 2 is attached. The endoscope 1 is provided with a viewing channel (not shown), which terminates at a lens on the distal face of the endoscope 1. The endoscope 1 is further provided with a working channel 3 and a suction channel 4, the proximal end of the suction channel 4 being connected to a source of vacuum (not shown).

The sewing device 2 includes a tube 5, which communicates with the suction channel 4, and has a plurality of perforations 6 therein. The perforations 6 communicate with an upwardly open vacuum chamber 7 formed in the sewing device 2.

A hollow needle 8 is mounted in the working channel 3 and has a beveled tip extending into the sewing device 2. The needle 8 has a channel 9 extending therethrough, with a flexible, wire-wound cable 10 attached to the rear of the needle 8. A center wire 11 extends within the cable 10, along the entire length thereof, and is longitudinally movable with respect thereto. The wire 11 is configured to be longitudinally movable within the channel 9 and, in the position shown in FIG. 1, the forward end portion of the wire 11 extends into the rear end portion of the channel 9.

A thread carrier or tag 12 (FIG. 1A) is slidably and releasably mounted in the channel 9. The tag 12 is hollow and has an aperture 13 extending through the sidewall thereof. One end of a thread 14 is secured to the tag 12 after passing through the aperture 13 and being tied in a knot 15 of sufficient size to prevent the thread 14 from slipping out of the tag 14.

A hollow head portion 16, defining a chamber 20 therein, is provided at the distal end of the sewing device 2. A wall 17 is provided between the chamber 20 and the cavity 7, wherein an aperture 18 is formed in the wall 17. The aperture 18 has a diameter that is greater than an external diameter of the needle 8, and is aligned therewith. The clearance between the needle 8 and the aperture 18 must be sufficiently small to prevent stomach tissue from being forced through the aperture 18 and causing the needle 8 to jam. Also, FIG. 1 illustrates a portion of the patient's tissue 19, in which a stitch is to be formed.

In operation, suction is applied to the suction channel 4 and then to the vacuum chamber 7 through the perforations 6 in the tube 5. As shown in FIG. 2, a U-shaped portion 19a of stomach tissue 19 is sucked into the vacuum chamber 7. The needle 8 is then pushed through the U-shaped tissue portion 19a by distally extending the cable 10 and needle 8. After the needle 8 has been fully advanced through both folds of the U-shaped tissue portion 19a, the beveled tip of the needle 8 extends distally beyond the wall 17 and within the chamber 20 in the hollow head portion 16. Distal movement of the wire 11, which is slidably received within the cable 10, pushes the tag 12 out of the channel 9 and into the chamber 20, where the tag 12 rotates out of alignment with the aperture 18 and is captured in the chamber 20.

The wire 11 is then proximally withdrawn, followed by the proximal withdrawal of the cable 10, to withdraw the needle 8 from the U-shaped tissue portion 19a. The suction is then discontinued, allowing the U-shaped tissue portion 19a to be released from the vacuum cavity 7.

As shown in FIG. 3, the released tissue is left with a suture thread 14 passing through the two layers of tissue that form the U-shaped fold 19a. One end of the suture thread 14 is joined to the tag 12 that remains captured in the chamber 20 and the other end of the suture thread 14 extends through the patient's esophagus and out of the mouth. Finally, the endoscope 1 and sewing device 2 are withdrawn from the patient. In so doing, the thread 14 is pulled partially through the tissue portion 19a, as the captured tag 12 is withdrawn proximally and brought outside the patient. With both ends of the thread 14 outside of the patient, the thread 14 is knotted and the knot endoscopically pushed down to the suture site and severed by an endoscopic knot pusher.

The '663 patent to Mills et al, as well as the '209 and '189 published patent applications of Gambale et al., like the device disclosed by the '153 patent to Swain et al., each disclose endoscopic apposition devices wherein the suture thread is retained proximal of the vacuum chamber prior to being threaded through the fold of stomach tissue. Each of these approaches presents certain problems. For example, with each, once the suture thread is passed through the fold of stomach tissue, the suture thread is not retained in a taut manner and may interfere with subsequent sewing or suturing procedures. Additionally, the vacuum channels for each of the conventional apposition devices are provided in the bottom or floor of their respective vacuum chambers. As such, the stomach tissue sucked into vacuum chamber can have a dimpled form. Therefore, the stomach tissue may not be securely retained in the vacuum chamber.

Furthermore, a problem exists in that several conventional devices require the device to be withdrawn from the patient after each stitch or suture made with a single-stitch device. The use of such devices is time consuming, cumbersome, and of some risk to the patient, due, for example, to the multiple intubations and danger of perforations to the esophagus. Also, the patient is required to be kept under sedation for a relatively long period of time.

SUMMARY OF INVENTION

The present invention provides an endoscopic stomach tissue apposition device capable of securing a plurality of tissue sites together with a single intubation of an endoscope carrying the apposition device at the distal end of the endoscope into the stomach of the patient. To position the suture in the appropriate locations, the apposition device may be releasably secured to the distal end of any suitable endoscope. The apposition device includes a tissue vacuum chamber that captures a section of stomach tissue therein, nesting carrier and punch needles that can extend across the vacuum chamber, and a tag that is joined to a suture to prevent the suture from falling out of the apposition device.

According to one aspect of the present invention, the apposition device is secured to the distal end of a flexible endoscope, which may be of the flexible or rigid type of endoscope. The endoscope is provided with a working channel and a vacuum channel that is connected to a vacuum source. Ideally, the vacuum channel comprises an internal channel within the apposition device and has a distal end that terminates at a vacuum chamber.

In one embodiment, a first or carrier needle having a hollow, beveled tip extending toward the vacuum chamber is disposed in the working channel. The beveled tip of the carrier needle is configured to receive a relatively shorter second or punch needle disposed within a holding chamber located on the distal end of the endoscope, on the opposite or distal side of the vacuum chamber. The punch needle also has a beveled tip that corresponds to the beveled tip of the carrier needle and is configured to receive the beveled tip of the carrier needle therein.

A holding channel is provided, for example, coaxial to the working chamber. Accordingly, when actuated, the carrier needle travels across the vacuum chamber and enters the holding channel. A release channel is located directly above the holding channel in a vertical direction relative to a bottom surface of the vacuum chamber. In one embodiment, a holding mechanism is located in the release channel and includes a pivotable key, which has a cam profile, a slotted member, which has a vertically extending slot incorporated therein to receive a pivot end of the key, and a biasing member.

The biasing member of this embodiment includes a cylinder slidably supported by first and second support struts, which include apertures formed therein that are configured to slidably receive the cylinder. The cylinder includes a stop protruding therefrom, at a location on the cylinder that is constantly intermediate the support struts. An elastic coil is wound around the cylinder in a spiral manner, such that a first end of the coil is constantly engaging the stop and a second end engages the support strut located at the distal end of the endoscope.

According to an aspect of the invention, an endoscopic tissue apposition device is provided that reduces the number of intubations required to attach or repair internal tissue by a tissue securement mechanism that uses a suture.

According to yet another aspect of the invention, an endoscopic apposition device is provided that is simple and economical to fabricate and use.

According to another aspect of the invention, a tissue apposition device is provided having longitudinal flexibility that is easily navigable through a natural body lumen while mounted at the distal end of an endoscope.

And yet another aspect of the invention provides a method of joining stomach tissue that comprises capturing at least two areas of tissue simultaneously to delivery tissue securement device through the areas of tissue to join them together.

Additional advantages and novel features of the invention will be set forth in part in the description that follows, and in part will become more apparent to those skilled in the art upon examination of the following or upon learning by practice of the invention.

BRIEF DESCRIPTION OF DRAWINGS

The foregoing and other aspects of the present invention will be appreciated more fully from the following description, with reference to the accompanying drawings wherein:

FIG. 4A is a perspective view of an isolated punch needle;

DETAILED DESCRIPTION OF THE PREFERRED EMBODIMENT

The present invention provides an endoscopic stomach tissue apposition device capable of securing a plurality of tissue sites together with a single intubation of an endoscope carrying the apposition device at the distal end of the endoscope into the stomach of the patient. To position the suture in the appropriate locations, the apposition device may be releasably secured to the distal end of any suitable endoscope. The apposition device includes a tissue vacuum chamber that captures a section of stomach tissue therein, nesting carrier and punch needles that can extend across the vacuum chamber, and a tag that is joined to a suture to prevent the suture from falling out of the apposition device.

Figure 1:
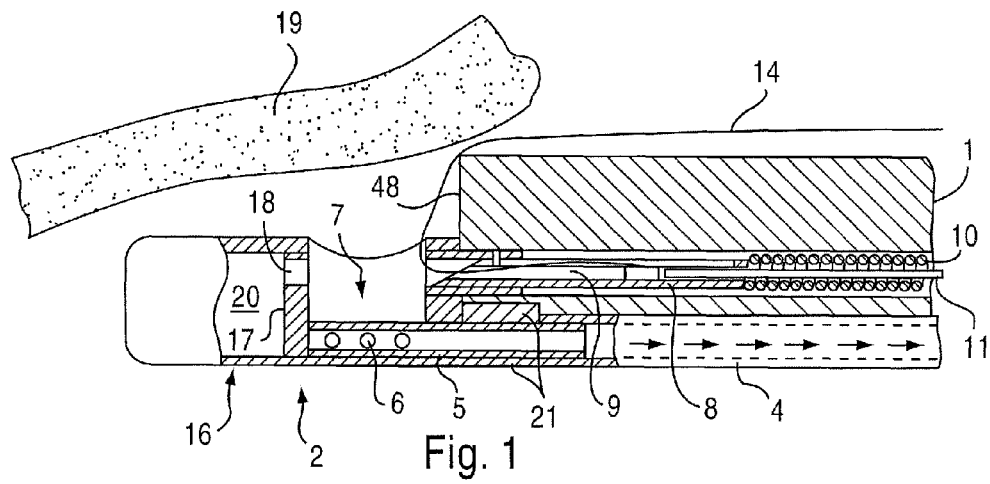
FIGS. 1-3 show successive steps in the operation of a conventional endoscopic apposition device.
Figure 1A:
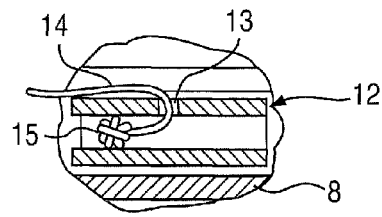
Figure 2:
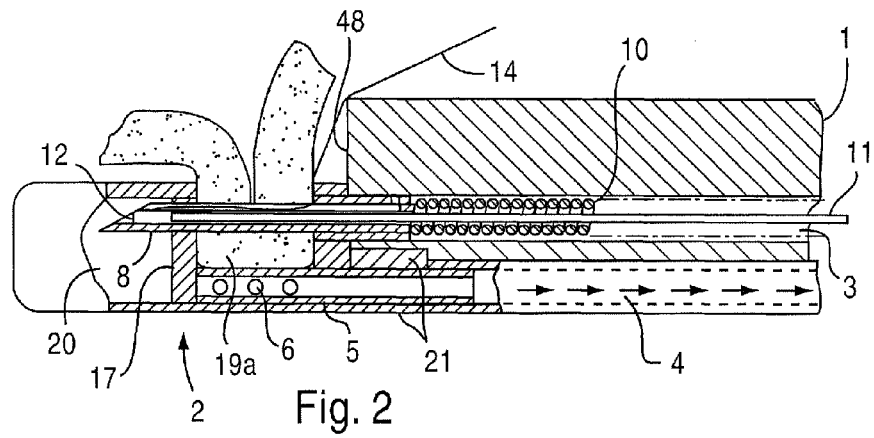
Figure 3:
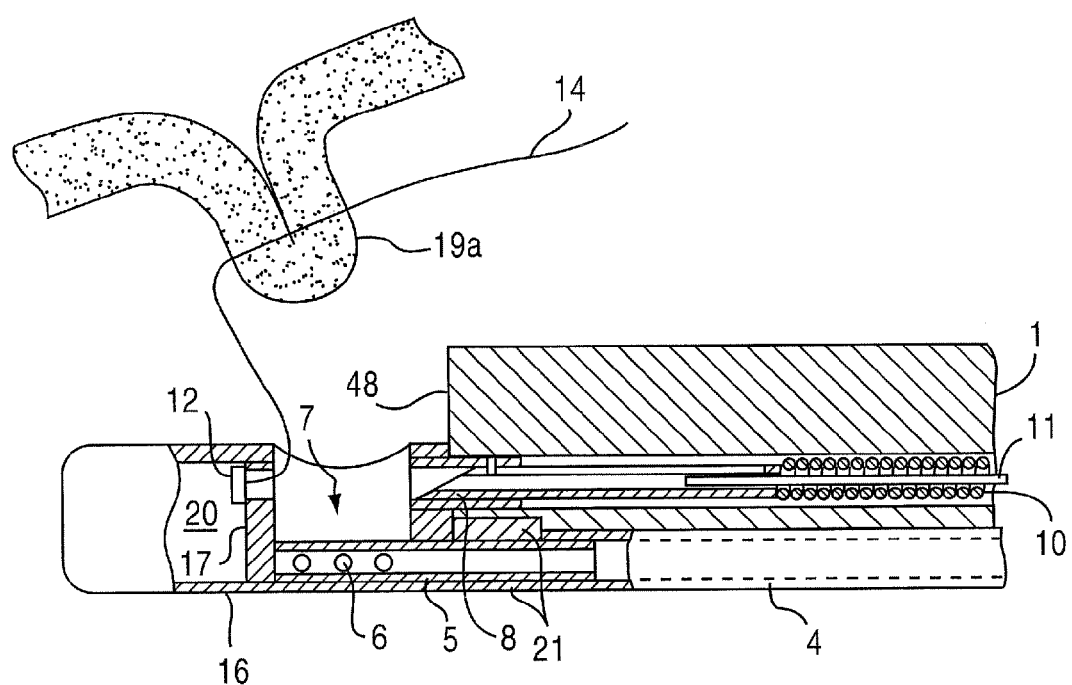
Figure 4:
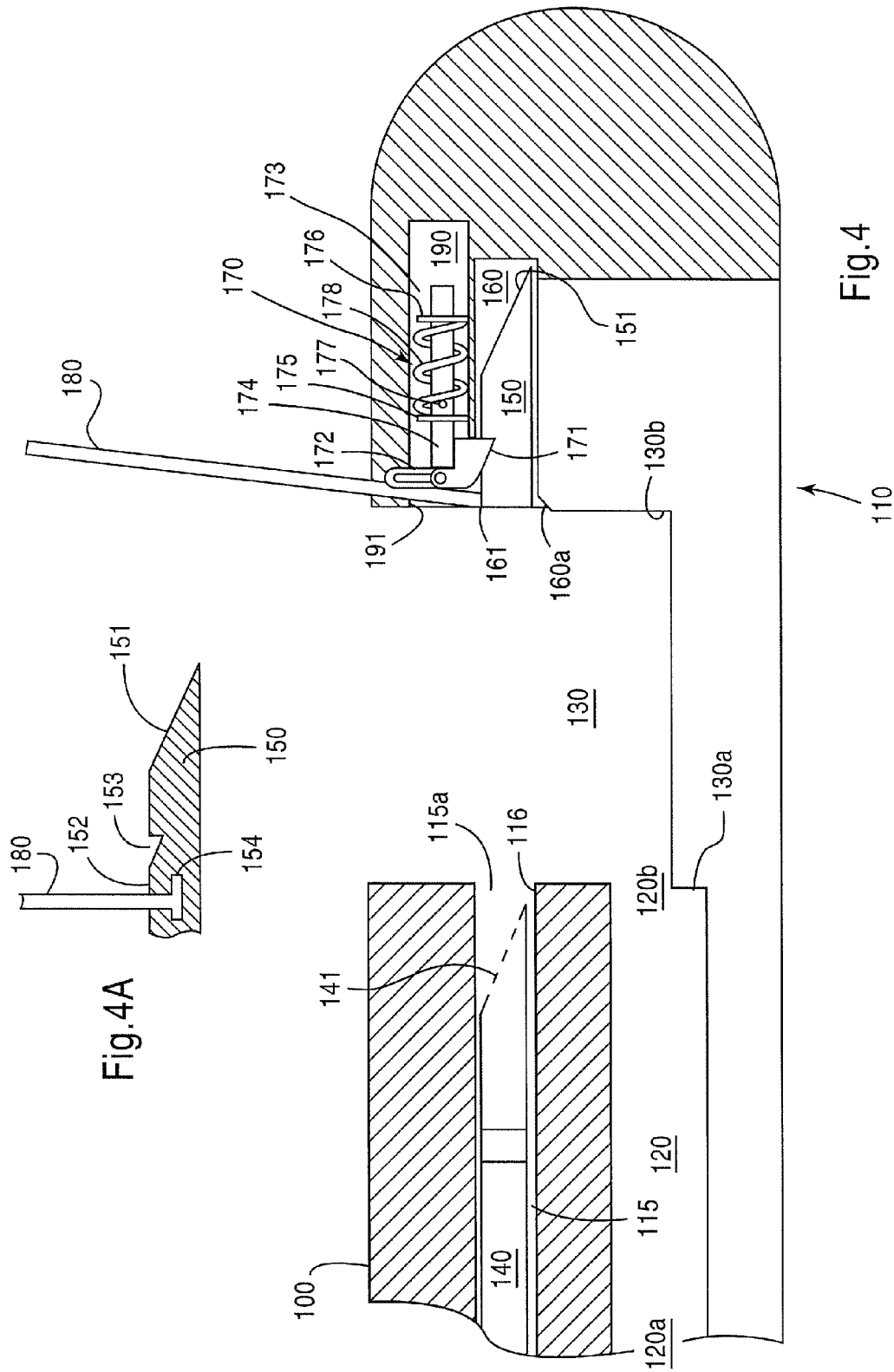
FIG. 4 is a schematic diagram of an apposition device having a carrier needle in a retracted position according to an embodiment of the present invention.

FIG. 4 shows the distal end of a flexible endoscope 100, on which an apposition device 110 according to the present invention is attached. The endoscope 100 is provided with a viewing channel (not shown) which terminates at a lens (not shown) on the distal face of the endoscope 100. The viewing channel and lens are conventional features well known in the art of endoscopic devices.

The endoscope 100 is also provided with a working channel 115 and a vacuum channel 120, wherein the proximal end 120a of the vacuum channel 120 is in communication with a vacuum source (not shown). Although the vacuum channel 120 may comprise a separate tube that runs exterior to the endoscope 100, rather than an internal channel as shown, in one embodiment it is preferable that the vacuum channel 120 include an internal channel and have a distal end 120b that terminates at a proximal vertical wall 130a of a vacuum chamber 130, as shown in FIG. 4, for reasons that will be provided below.

In exemplary arrangements, as shown in FIG. 4, a first or carrier needle 140 having a beveled tip 141 extending toward the vacuum chamber 130 is disposed in the working channel 115. The beveled tip 141 of the carrier needle 140 is hollow and configured to receive a relatively shorter second or punch needle 150 located on the distal end of the endoscope 100 on the opposite or distal side of the vacuum chamber 130 relative to the carrier needle 140. The punch needle 150 has a beveled tip 151 that corresponds to the beveled tip 141 of the traveling needle 140 and is configured to receive the beveled tip 141 of the carrier needle 140 therein. The punch needle 150 is held within a holding channel 160 located on the distal end of the endoscope 100 by a holding mechanism 170.

FIG. 4A shows an enlarged view of the punch needle 150 of the embodiment of FIG. 4, which includes an aperture 152 and a notch 153. The aperture 152 is configured to receive a suture or thread 180 thereinto, wherein a diameter of the aperture 152 is greater than a diameter of the suture 180. A tag or other retaining feature 154 is affixed to the end of the suture 180 and configured to be of a size greater than the diameter of the aperture 152, wherein the tag or other retaining feature 154 cannot pass through the aperture 152. The assembly of the suture 180 and tag 154 is securely retained by the punch needle 150 throughout the surgical procedures in which the apposition device 110 is used. The notch 153 is configured to be releasably engaged, for example, by a pivotable key 171, as shown in FIG. 4.

The present invention includes a hold and release mechanism. As shown in the exemplary embodiment of FIG. 4, the holding channel 160 is coaxial to the working chamber 115. An aperture 116 located at a distal end 115a of the working chamber 115 is directly opposite an aperture 161 at a proximal end 160a of the holding channel 160. Accordingly, when actuated, the carrier needle 140 traverses and eventually spans the vacuum chamber 130, and enters the holding channel 160.

A release channel 190 is located directly above the holding channel 160 in a normal (or perpendicular) direction relative to a bottom surface of the vacuum chamber 130. An aperture 191 at a distal end 190a of the release channel 190 is located in a corresponding location adjacent the aperture 161 for the holding channel 160. However, as shown in FIG. 4, the release channel 190 has a longitudinal length that is greater than a longitudinal length of the holding channel 160 for reasons provided below.

The holding mechanism 170 is located in the release channel 190 and includes the pivotable key 171, which has a cam profile, a slotted member 172, which has a vertically extending slot 172a incorporated therein to receive a pivot end of the key 171, and a biasing member 173. The biasing member 173 includes a cylinder 174 slidably supported by first and second support struts 175 and 176. The support struts 175 and 176 include apertures formed therein that are configured to slidably receive the cylinder 174 therein.

The cylinder 174 includes a stop 177 protruding therefrom at a location on the cylinder 174 that is constantly intermediate the support struts 175 and 176. A biasing member 178, such as, for example only, an elastic coil, is wound around the cylinder 174 in a spiral manner such that a first end of the coil 178 is constantly engaging the stop 177 protruding from the cylinder 174 and a second end of the coil 178 engages the second support strut 176 located at the distal end of the endoscope 100. The notch 153 defined in the punch needle 150, the key 171, the aperture 161, and the slotted member 172 define a reloading mechanism which prepares the device 110 for the next stitch to be sewn.

FIGS. 4-10 will now be used to explain how the apposition or sewing device 110 operates to join neighboring sections of stomach tissue together using the exemplary device of FIGS. 4 and 4A.

Referring to FIGS. 4 and 4A, the apposition device 110 of the present invention is attached to the end of a flexible or rigid endoscope 100. The carrier needle 140 is maintained in a first position within the working channel 115. During the first position, the punch needle 150 is maintained within the holding channel 160 by the pivotable key 171 of the holding mechanism 170 engaging the notch 153 of the punch needle 150. At the same time, the suture 180 passing through the aperture 152 in the punch needle 150 is retained therein by the tag 154. Also, the first end of the cylinder 174 is free from or not engaging key 171.

Figure 5:
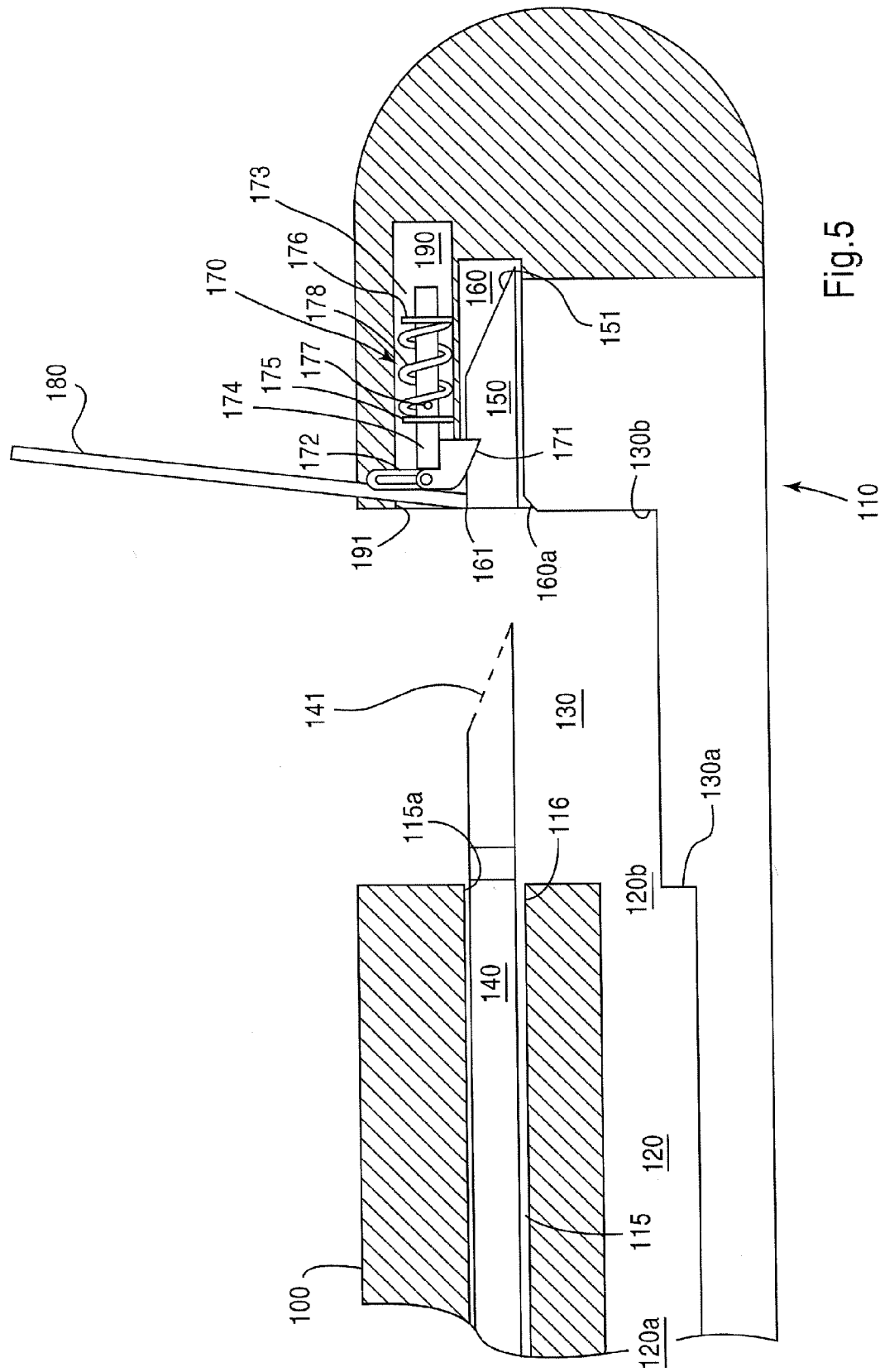
FIG. 5 is a schematic diagram showing the carrier needle in a slightly extended position in accordance with an embodiment of the present invention.

Then, as shown in FIG. 5, the carrier needle 140 is actuated and the beveled tip 141 of the needle 140 enters the vacuum chamber 130. Meanwhile, the punch needle 150 continues to be maintained in the holding channel 160 by the key 171. Further, the cylinder 174 continues to be from engaging or contacting the key 171.

Upon totally crossing the vacuum chamber 130, the beveled tip 141 of the carrier needle 140 enters and is engaged by the punch needle 150. See FIG. 6. Then, retraction of the nested carrier and punch needles 140 and 150 begins, such that the needles 140 and 150 are drawn back toward the working channel 115, and the key 171 is pivotably and slidably disengaged from the notch 153 of the punch needle 150. When the needles 140 and 150 initially are retracted, the key 171 begins traveling up the slotted member 172, wherein the cam of the key 171 contacts the end of the cylinder 174.

Figure 6:
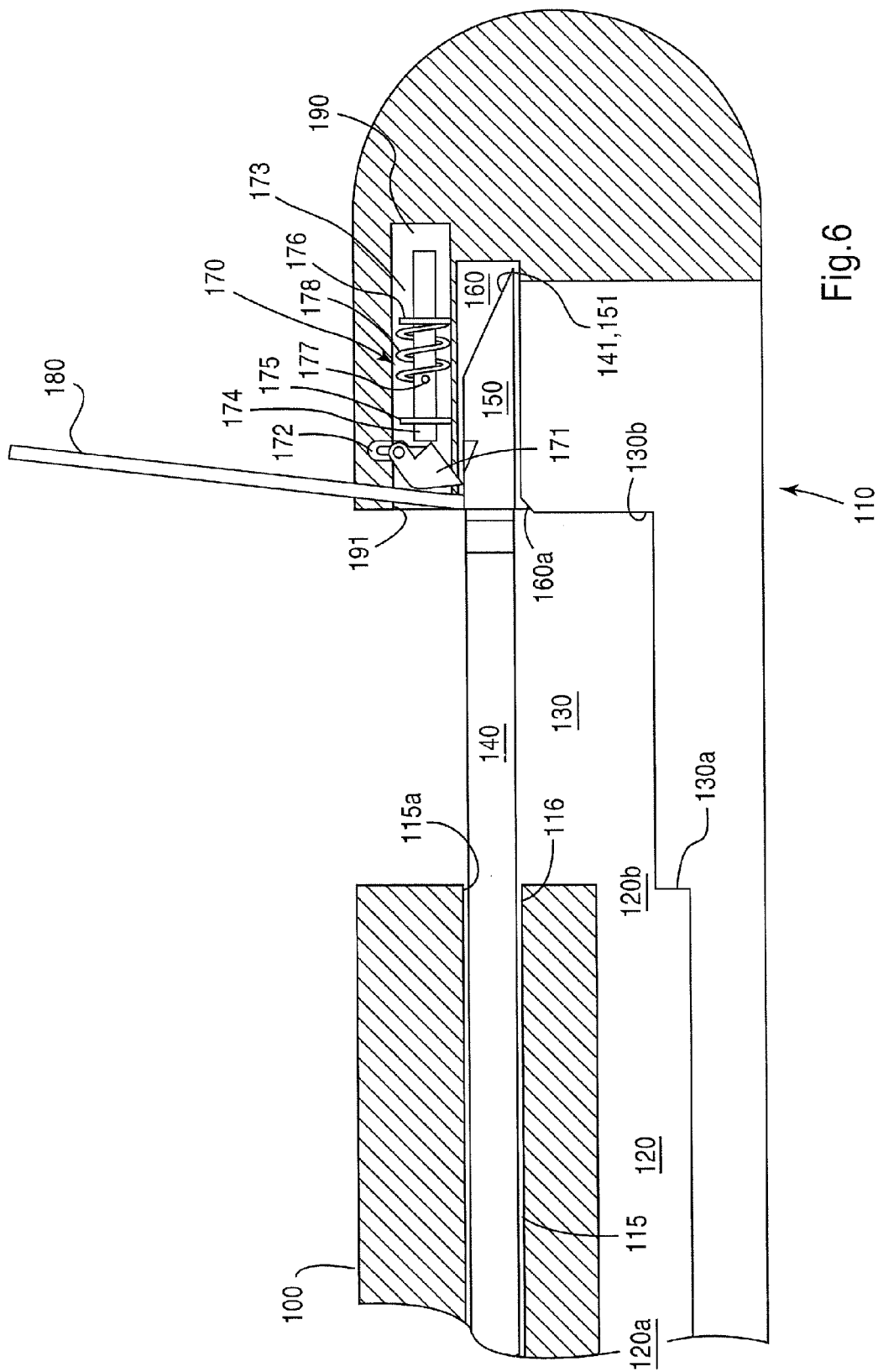
FIG. 6 is a schematic diagram showing the carrier needle nested within the punch needle in accordance with an embodiment of the present invention.
Figure 7:
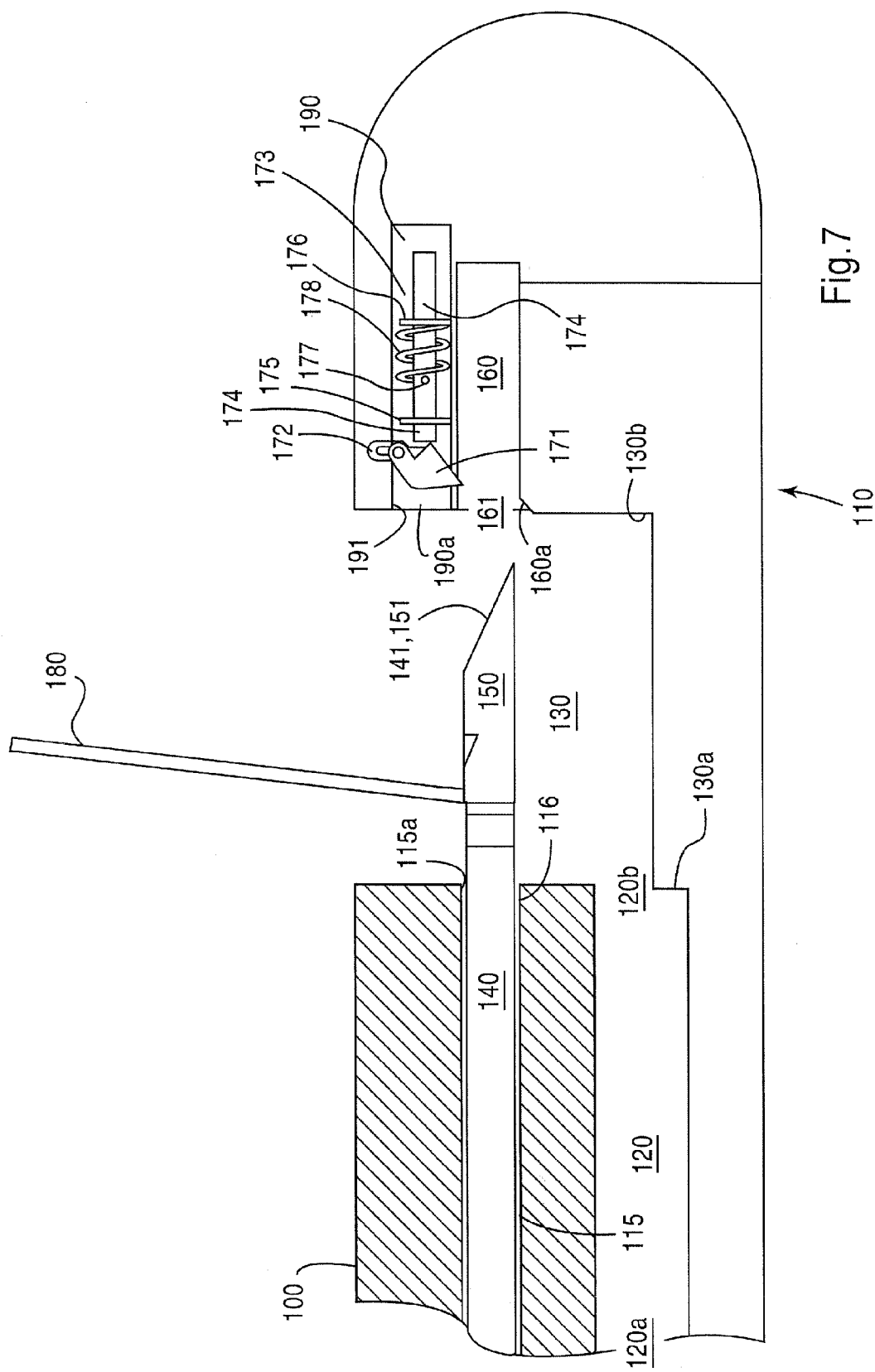
FIG. 7 is a schematic diagram showing the nested carrier and punch needles being retracted in accordance with an embodiment of the present invention.
Figure 8:
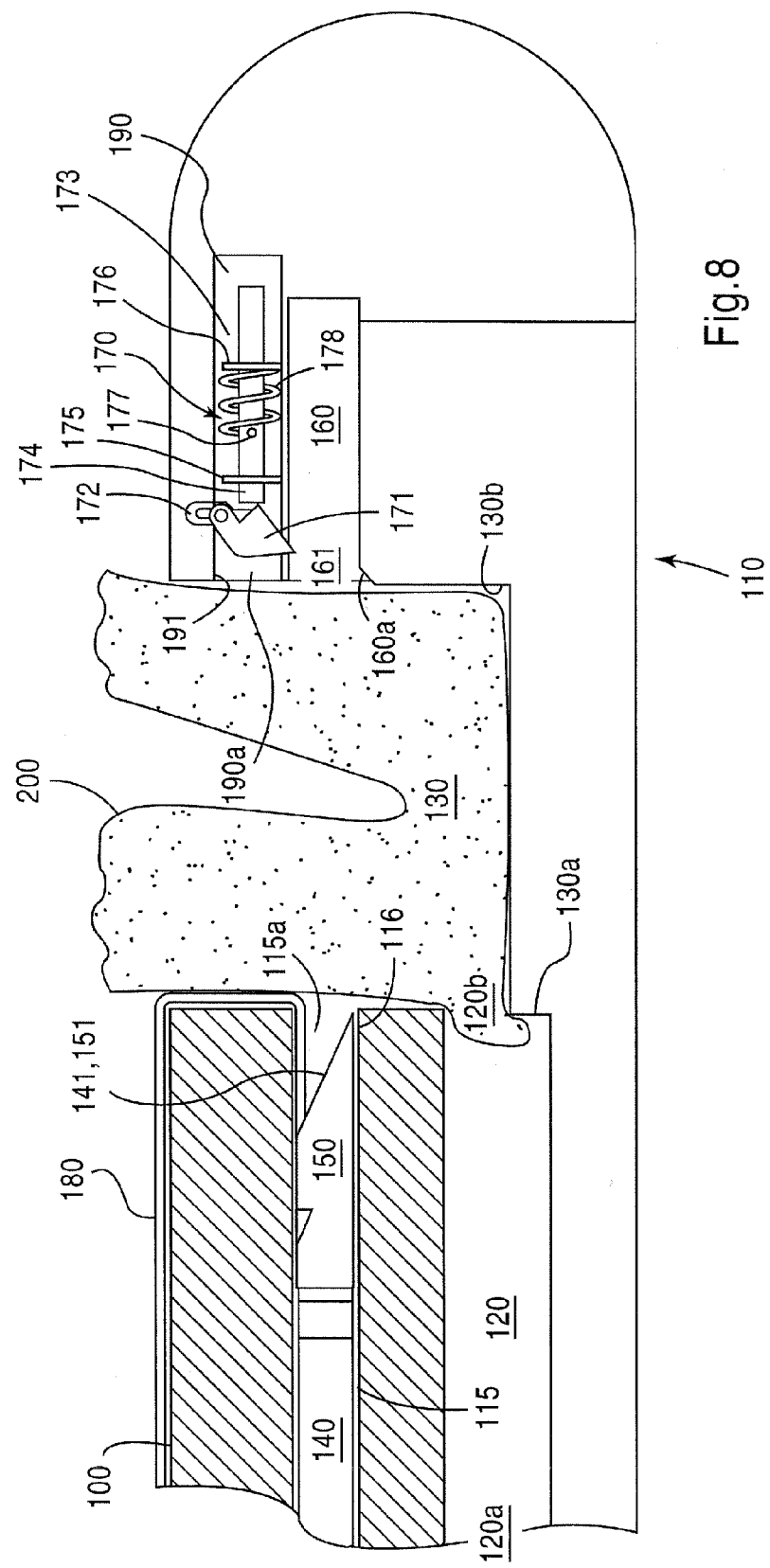
FIG. 8 is a schematic diagram showing a U-shaped section of stomach tissue being sucked into the vacuum chamber and vacuum channel in accordance with an embodiment of the present invention.

According to the exemplary embodiment of FIG. 4, the cam profile drives the cylinder 174 toward the distal most end of the endoscope 100 (toward the right as viewed in FIG. 6). As the cylinder 174 is being driven distally (i.e., to the right as viewed in FIG. 6), the stop 177 extending away from an outer surface the cylinder 174 engages a first end of the coil 178 while the second end of the coil 178 presses up against the support strut 176. The continued driving of the cylinder 174 by the cam profile of the key 171 results in the compression of the coil 178 between the moving stop 177 and the support strut 176. The distal most end of the cylinder 174 extends into the distal end of the release channel 190 and beyond the distal end of the holding channel 160. See FIG. 7.

Once the nested needles 140 and 150 are retracted proximally to be disposed within the working channel 115, the vacuum source (not shown) is turned on, such that a vacuum pressure is created in the vacuum chamber 130 via the vacuum channel 120. As a result, neighboring sections of stomach tissue are drawn into the vacuum chamber 130 and distal end 120b of the vacuum channel, via the vacuum pressure, to form a U-shaped portion of tissue 200 within the vacuum chamber 130. See FIG. 8. Meanwhile, the biasing member or coil 178 continues to bias the stop 177 away from the distal end of the endoscope 110, wherein the cylinder 174 is driven toward the aperture 190a of the release channel 190.

Figure 9:
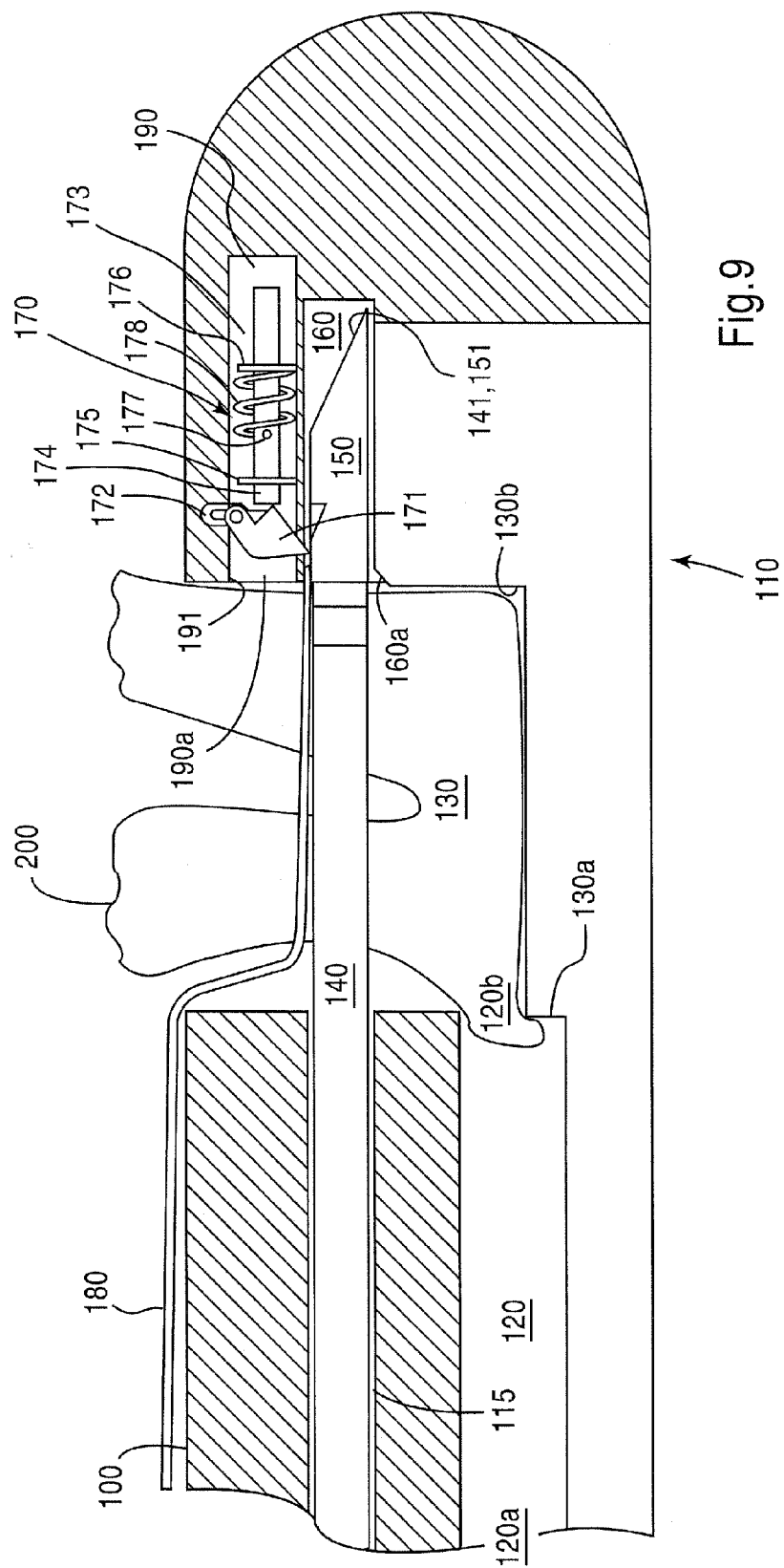
FIG. 9 is a schematic diagram showing the carrier and punch needles piercing the U-shaped section of stomach tissue in accordance with an embodiment of the present invention.

The nested needles 140 and 150 then pierce the U-shaped portion of tissue 200 when the nested needles 140 and 150 are actuated or driven back across the vacuum chamber 130 toward the holding channel 160 in the distal end of the endoscope 100. As shown in FIG. 9, the suture 180 is threaded through the passage formed in the U-shaped portion of tissue 200 by the tip 151 of the punch needle 150. As explained above, the suture 180 is securely maintained in the punch needle 150 by the tag 154 affixed to the end of the suture 180.

Once the punch needle 150 enters the holding channel 160, the carrier needle 140 is released from the punch needle 150 and is retracted back into the working channel 115. Then, because the carrier needle 140 is no longer nested within the punch needle 140, the outer surface of the carrier needle 140 does not prevent the key 171 from entering the notch 153 of the punch needle 150. As such, the key 171 slides down the slotted member 172, such that a tip of the key 171 drops or extends into the holding channel 160, whereupon the key 171 engages the notch 153 of the needle 150 and secures the needle 150 within the channel 160.

Figure 10:
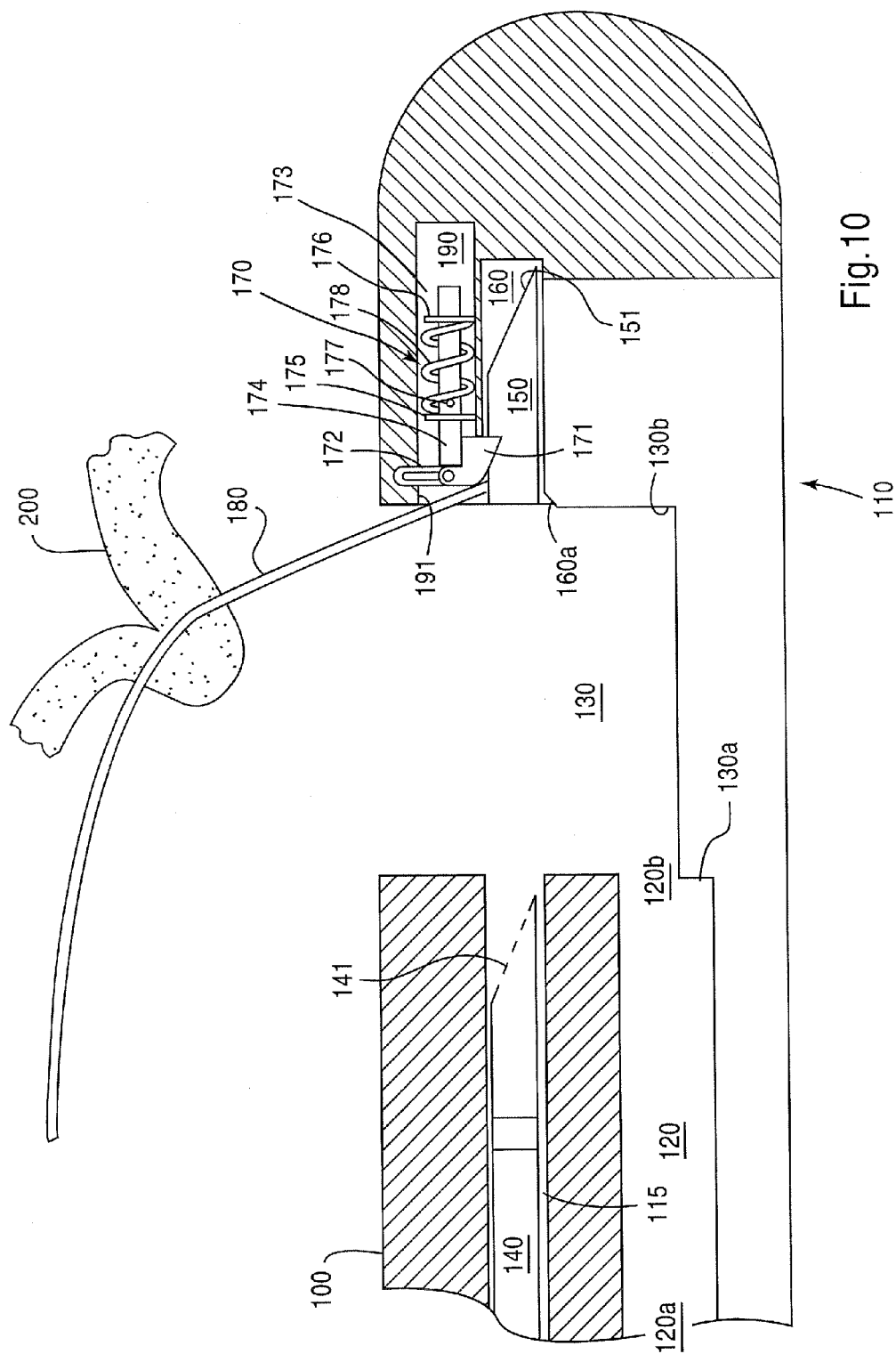
FIG. 10 is a schematic diagram showing the sutured section of stomach tissue being retained by a suture and the carrier and punch needles in their respective original stations in accordance with an embodiment of the present invention.

At this time, the vacuum source is turned off and the sutured U-shaped portion of tissue 200 retracts from the vacuum chamber 130, with the suture 180 passing therethrough, as shown in FIG. 10.

As will be made clearer from the exemplary procedure illustrated in FIGS. 11-16, the apposition device 110 is then moved to another section of the stomach and the steps discussed above with regards to FIGS. 4-10 repeated.

For example only, and in no way intended to limit the scope of the present invention or the various additional types of procedures during which the invention can be used, the apposition device 110 of the present invention being used during a bariatric surgical process will now be discussed in order to provide a better understanding of the many ways in which the invention may be operated.

Initially, the patient is anaesthetized and positioned to lay oblique relative to a working surface, such as, for example, a surgical table. The apposition device 110 is positioned near the patient's gastric esophagus joint using a guide wire. The guide wire is then removed.

Figure 11:
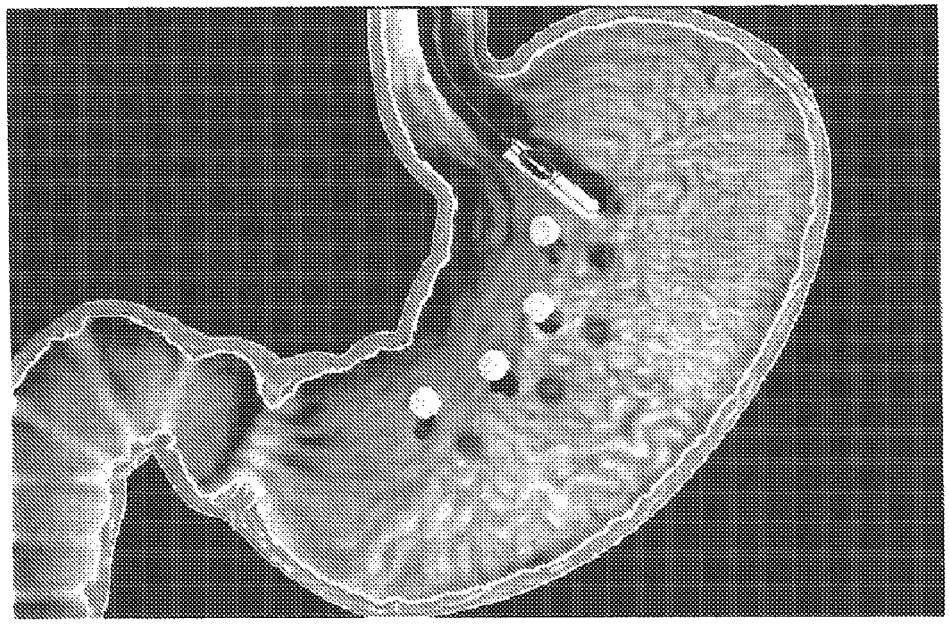
FIGS. 11-16 illustrate the sequential steps of an exemplary process for suturing a stomach using the apposition device according to the embodiments of the present invention.

The bariatric surgical process is typically applied to the stomach of a human patient. In general, a human stomach has a preceding face, a posterior face, and a greater curvature extending therebetween. During such a procedure, the greater curvature of the stomach is closed with the suture, which is ideally a non-absorbable cord that will extend from the near edge of the propyloric cavern to the gastric fundus. As illustrated in FIG. 11, the suture is to be applied at alternating points that are approximately 10 centimeters from one another.

Preferably, the bariatric surgical procedure is carried out with an endoscope 100 having an apposition device 110 attached to the distal end thereof. As shown in FIG. 11, the endoscope 100 and apposition device 110 are inserted through the esophagus into the stomach of a patient. The device 110 is positioned over a plurality of alternating points, where U-shaped portions of stomach tissue 200 are sutured or sewn together using the device and method described above in conjunction with FIGS. 4-10.

Figure 16:

As shown in FIGS. 11-15, the stomach tissue at the alternating points are sequentially sutured together to define the revised stomach of FIG. 16, which has a significantly reduced volume than before the procedure, as the anterior and posterior walls of the stomach are brought together. For example, it is estimated the process can be used to reduce the size of the gastric camera by approximately 50% top 60% with an approximately one hour procedure.

Figure 12:
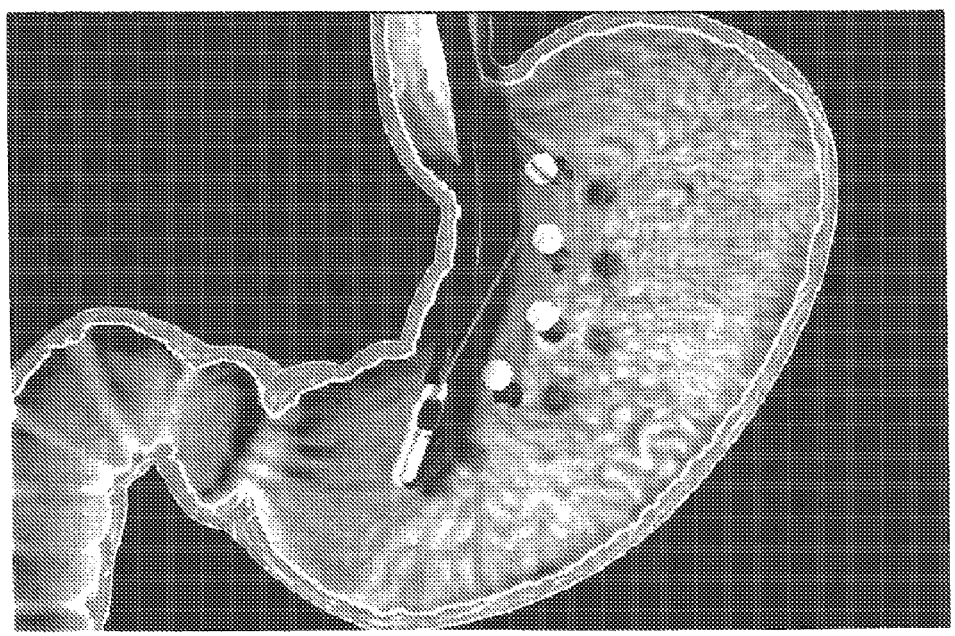
Figure 13:
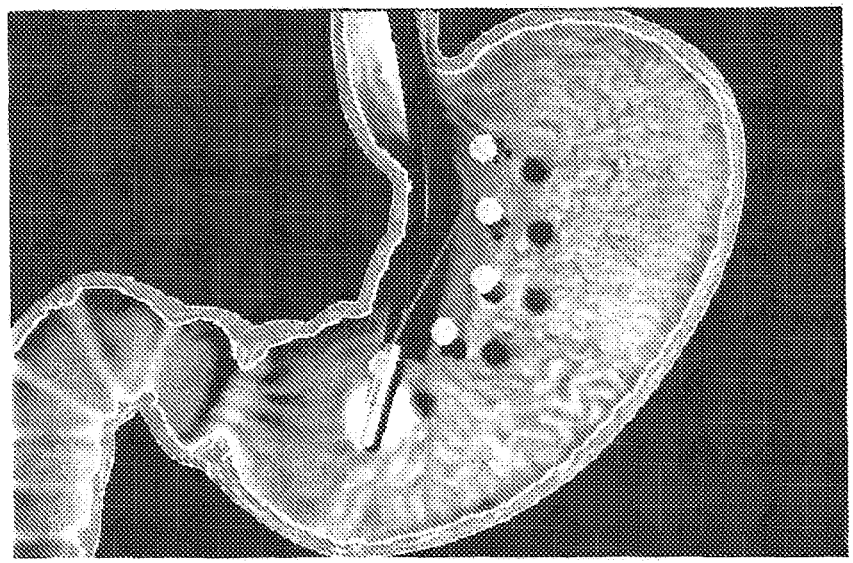
Figure 14:
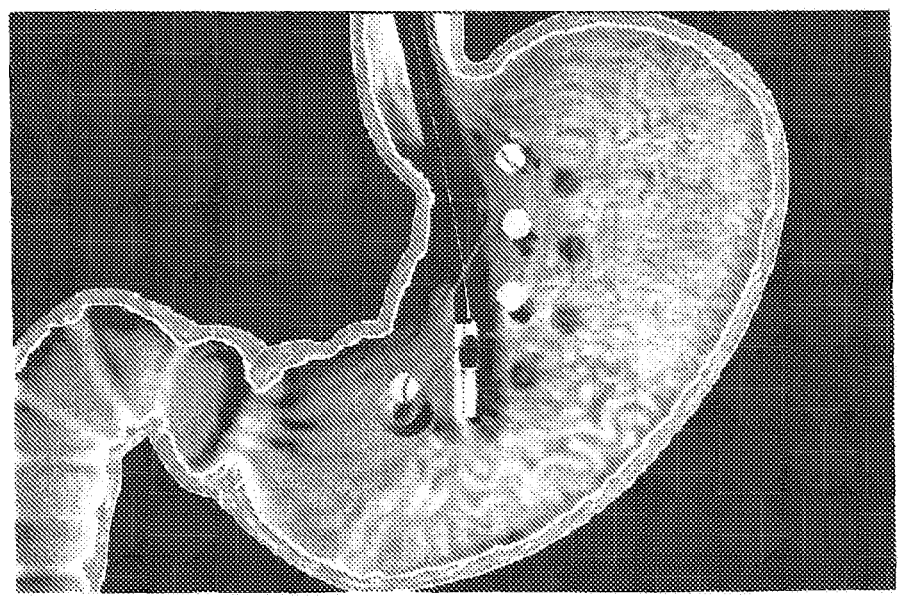
Figure 15:
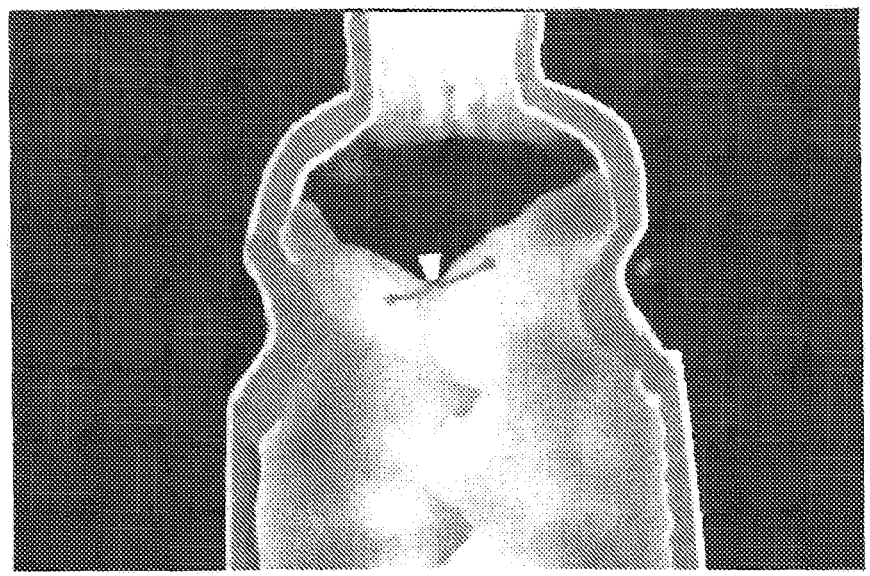

The first stitch is sewn approximately 2 centimeters (cm) from the gastric esophagus joint on the back face of the gastric fundus (FIG. 11). The apposition device 110 is then moved forward approximately 10-12 cm toward a gastric angle on the same back face, and the next stitch is sewn as shown and described above in conjunction with FIGS. 4-10 (FIG. 12). In order to maintain a sufficient length of the suture 180 within the stomach, the device 110 is moved away from the gastric wall and towards the pylorus (FIG. 13). The apposition device 110 is then moved upwardly toward the gastric esophagus joint, in front of the second stitch towards the rear wall of the stomach (FIG. 14). The next stitch is sewn as shown and described above in conjunction with FIG. 4-10.

The procedure is repeated wherein subsequent stitches are sewn in an alternatingly left, then right, side manner and in an upward direction approximately 1 to 1.5 cm apart until reaching a position on the opposite side of the stomach from the first stitch, about 2 cm from the gastric esophagus joint. The opposite ends of the suture 180 are then drawn together (FIG. 15), wherein the fundus space and gastric body size are reduced (FIG. 16).

Once the procedure is completed, the apposition device 110 is withdrawn from the patient and the ends of the suture 180 tied together in a knot or retained together by a suitable retaining device, such as, a biodegradable stomach clamp or clip, that is then pushed back into the stomach of the patient, with excess suture then removed. See FIG. 15.

It is anticipated that the process be an ambulatory process that is carried out using propofol intravenous anesthesiology, whereupon the patient can expect to consume liquids as soon as six hours after the procedure is completed.

While there has been described what is at present considered to be a preferred embodiment of the present invention, it will be understood that various modifications may be made thereto, and it is intended that the appended claims cover all such modifications as fall within the true spirit and scope of the invention.

For example, the aforementioned holding mechanism 170 is merely an exemplary embodiment of structural components that maybe used to intermittently retain the punch needle in the holding channel 160. It is within the scope of the invention to use any known or later developed system for performing such a function. For example, the punch needle 150 may be retained in the holding channel 160 via friction, gravity, magnetic forces, electromagnetic forces, a solenoid member, and the like. Moreover, the cam on the key 171, struts 175 and 176, as well as the cylinder 174, stop 177, and coil 178 elements can be omitted so long as a suitable manner of facilitating the key 171 and notch 153 of the punch needle 150 to intermittently engage and disengage from each other is provided.

What is claimed is:

1. An endoscopic tissue apposition device, comprising:
   a device body having a first end portion and a second end portion;
   a vacuum chamber within the device body for receiving tissue drawn therein with a vacuum, the vacuum chamber being located between the first end portion and the second end portion;
   a carrier needle retractable within the first end portion of the device body and traversable across the vacuum chamber to the second end portion of the device body, the carrier needle including a beveled tip;
   a punch needle engageable with the second end portion of the device body, wherein the punch needle is configured to receive the carrier needle; and
   a hold and release mechanism configured to intermittently retain the punch needle in the second end portion of the device body, the hold and release mechanism including a holding channel and a release channel, the holding channel configured to releasably hold the punch needle therein, the release channel including a holding mechanism therein, the holding mechanism including a key having a pivot end, a slotted member having a vertically extending slot configured to slidably receive the pivot end of the key therein, and a biasing member,
   wherein a suture is attachable to the punch needle, and
   wherein the punch needle with the attached suture is traversable across the vacuum chamber upon the carrier needle being received within the punch needle.

2. The apposition device according to claim 1, wherein the punch needle includes a beveled tip.

3. The apposition device according to claim 2, wherein the beveled tip of the punch needle corresponds to the beveled tip of the carrier needle.

4. The apposition device according to claim 2, wherein the punch needle is hollow.

5. The apposition device according to claim 1, further comprising a vacuum line communicating with the vacuum chamber for applying a vacuum to the vacuum chamber.

6. The apposition device according to claim 1, wherein the release channel has a longitudinal length greater than a longitudinal length of the holding channel.

7. The apposition device according to claim 1, wherein the punch needle further comprises:
   a notch configured to receive the key therein to prevent the punch needle from sliding out of the holding channel; and
   a suture aperture.

8. The apposition device according to claim 7, wherein a suture passes through the suture aperture of the punch needle.

9. The apposition device according to claim 8, further comprising a tag attached to a free end of the suture, the tag being configured to be larger than the suture aperture to prevent the suture from falling out of the punch needle.

10. The apposition device according to claim 9, wherein the biasing member comprises:
    a cylinder having a stop protruding radially away from an outer surface of the cylinder;
    at least one support strut having a through-hole formed therein through which the cylinder is longitudinally advanced; and
    a coil wound around the outer surface of the cylinder.

11. The apposition device according to claim 10, wherein a first end of the coil engages the stop and a second end of the coil engages the second support strut.

12. The apposition device according to claim 11, wherein the key further includes a cam which urges the cylinder toward a distal end of the device when the key slides vertically upward as the punch needle is being removed from the holding channel and as the carrier needle is retracted back toward the working channel, and wherein the coil is compressed between the stop and second support strut.

* * * * *